(12) United States Patent
Bachmann

(10) Patent No.: US 8,821,513 B1
(45) Date of Patent: *Sep. 2, 2014

(54) NAVEL UMBILICAL CORD TAB

(76) Inventor: Jaycinth E. Bachmann, Port St. Lucie, FL (US)

(*) Notice: Subject to any disclaimer, the term of this patent is extended or adjusted under 35 U.S.C. 154(b) by 462 days.

This patent is subject to a terminal disclaimer.

(21) Appl. No.: 12/214,307

(22) Filed: Jun. 18, 2008

Related U.S. Application Data

(60) Provisional application No. 60/934,967, filed on Jun. 18, 2007.

(51) Int. Cl.
*A61B 17/50* (2006.01)

(52) U.S. Cl.
USPC ........................................ 606/131; 606/119

(58) Field of Classification Search
CPC ..... A61B 17/122; A61B 17/42; A61M 25/02; A61M 35/00; A61M 2025/0246; A61F 2013/1504; A61F 13/00
USPC ......... 606/116, 117, 119, 120, 125, 131, 151, 606/157; 604/289, 303, 385.01; 602/41, 42, 602/60, 61, 72, 78, 79; 128/846
See application file for complete search history.

(56) References Cited

U.S. PATENT DOCUMENTS

| | | | | |
|---|---|---|---|---|
| 3,016,056 A | * | 1/1962 | Jacobs | 606/117 |
| 3,674,032 A | * | 7/1972 | Minganti | 606/120 |
| 5,009,657 A | * | 4/1991 | Cotey et al. | 606/120 |
| 5,620,419 A | * | 4/1997 | Lui et al. | 604/116 |
| 5,667,516 A | * | 9/1997 | Allen | 606/120 |
| 6,318,371 B1 | * | 11/2001 | Tyszkiewicz | 128/859 |
| 6,875,200 B1 | * | 4/2005 | Ajagbe | 604/290 |
| 2002/0198535 A1 | * | 12/2002 | Watson et al. | 606/120 |

* cited by examiner

*Primary Examiner* — Ryan Severson
*Assistant Examiner* — Katherine M Shi
(74) *Attorney, Agent, or Firm* — Scully, Scott, Murphy & Presser, P.C.

(57) ABSTRACT

The navel umbilical cord tab is a method and apparatus provided for cleaning the navel and umbilical cord.
The navel umbilical cord tab placed around the navel with the umbilical cord protruding through the center orifice
The navel umbilical cord tab is engaged to maneuver, control, support, and protect the umbilical cord.
The navel umbilical cord tab allows for thorough cleaning of the navel and umbilical cord using cotton swabs with or without cleaning chemicals
The navel umbilical cord tab eliminates physical holding of the umbilical cord during the cleaning procedure.

12 Claims, 7 Drawing Sheets

NAVEL UMBILICAL CORD TAB

CROSS-REFERENCE TO RELATED APPLICATION

"Not Applicable"

STATEMENT REGARDING FEDERALLY SPONSORED RESEARCH OR DEVELOPMENT

"Not Applicable"

REFERENCE TO SEQUENCE LISTING, A TABLE, OR A COMPUTER PROGRAM LISTING COMPACT DISC APPENDIX

"Not Applicable"

BACKGROUND OF THE INVENTION

The subject matter of the claimed invention relates to cleaning of the baby's navel and umbilical cord. This invention eliminates physically holding of the umbilical cord and allowing for easy reach to trapped and hidden moisture in the navel and around the umbilical cord. This invention also shields the baby's skin from chemical used when cleaning the navel and umbilical cord.

The current and primitive way of cleaning the baby's navel and umbilical cord is by pinching the umbilical cord stump with the thumb and fore finger.

This current and primitive method is cumbersome and presents significant difficulties, such as:
a. The umbilical cord continuously slips out of one's grip;
b. The fear of hurting the baby exists while tugging on the umbilical cord in an effort to regain and enforce the grip.
c. One has poor access to trapped and hidden moisture in and around the umbilical cord which slows down the drying process and impedes early separation of the umbilical cord; and
d. The baby's skin is not protected from direct contact with chemicals used during the cleaning procedure.

Thus the need exists for an umbilical cord device to clean the navel and umbilical cord and more particular to engage in the control, support and protection of the umbilical cord during the cleaning procedure with features to:
a. Eliminate physically holding of the umbilical cord;
b. Control cord positioning;
c. Allow for easy access to remove trapped and hidden moisture in the navel and around the umbilical cord which enhances the drying process and promotes early separation of the umbilical cord; and
d. Further shield the baby's skin from chemical used when cleaning the navel and umbilical cord.

BRIEF SUMMARY OF THE INVENTION

The existing need to clean the umbilical cord has been satisfied with a navel umbilical cord tab. The umbilical cord tab is one unit that includes an upper and lower level which surrounds an interior orifice.

The lower level is likened to a pair of flange lips that extends around the periphery of the orifice.
  a. The lower level is a designated surface area that is placed around a baby's navel with the umbilical cord protruding through the orifice;
  b. The orifice employed substantially surrounds the umbilical cord; and
  c. The orifice measures 1 inch in diameter, a preferable size that is suitable to accommodate a navel and umbilical cord large or small.

As the cord is being cleaned, the lower level is used to maneuver the umbilical cord in different directions, making it easy to remove trapped and hidden moisture in the navel and around the umbilical cord. The upper level is fixedly mounted around the orifice of the lower level.

The upper level has sides that are upwardly extended.

The body of the upper level is in the shape of the letter "C."

As the navel and umbilical cord is being cleaned, the upper level upwardly extended sides are engaged in control, support and the protection of the umbilical cord.

In this vicinity where the upper level encircles the periphery of the orifice, a surface is formed. The surface area is in connection with the upwardly extended sides of the upper level and is
  a. Eliminates physically holding of the umbilical cord during the cleaning procedure;
  b. Engages in control, support and protection of the umbilical cord during the cleaning process;
  c. Exposes trapped and hidden moisture around the navel and umbilical cord; and promotes keeping the navel and umbilical cord dry which enhances early separation of the umbilical cord.
  d. Promotes keeping the navel and umbilical cord dry which enhances early separation of the umbilical cord.
In addition some other advantages of this invention are:
  a. The navel umbilical cord tab is easy to operate, safe and user friendly, and operable with both hands;
  b. The navel umbilical cord tab is reusable and can be washed then sanitized in dishwasher, bottle sterilizer or microwave; and
  c. The navel umbilical cord tab is made from polypropylene material, a non-absorbent plastic that is phthalates free.

BRIEF DESCRIPTION OF THE SEVERAL VIEWS OF THE DRAWING

Drawings of a preferred embodiment of the navel umbilical cord tab are annexed hereto so that the invention may be better and more fully understood FIG. 1 A perspective view of the navel umbilical cord tab in accordance with the present invention.

DETAIL DESCRIPTION OF THE INVENTION

Figure 1:
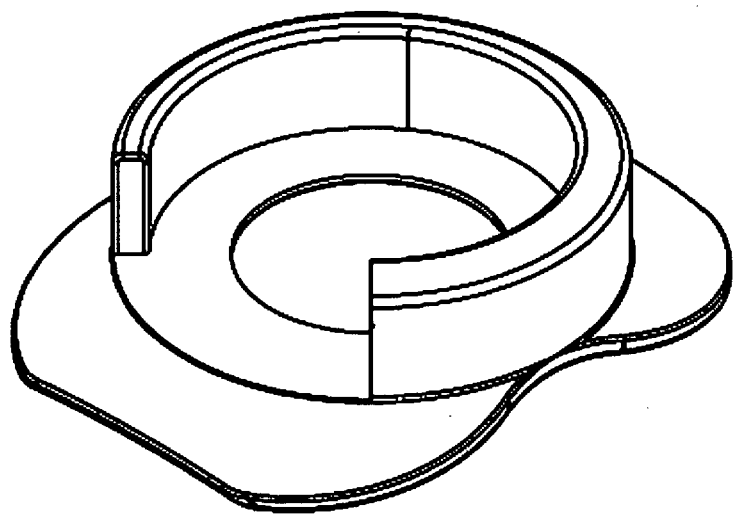

Referring to FIG. 1 the navel umbilical cord tab in accordance with the present invention.

The navel umbilical cord tab is a single unit manufactured by an injection molding process.

The preferred material used for this invention is polypropylene, a non-absorbent plastic that is "phthalates," free, and well known to those of ordinary skill in the art.

The navel umbilical cord tab FIG. 1 comprises of:
Lower level FIG. 3 and an upper level FIG. 2
FIG. 3 comprises the following sections:
A pair of open flanged lips 22a-22b.
A surface area 10
An orifice 25
The open flanged lips are adjacent from each other adjoining to a surface area 10
Surface area 10 borders orifice 25.
Orifice 25 measures approximately 1 inch in diameter. A preferable size that is suitable to accommodate a navel and umbilical cord up to 1 in diameter.
FIG. 3 The open flanged lips 22a-22b, orifice 25 and surface area 10 of the embodiment is the designated area that is placed on the baby's abdomen. Orifice 25 surrounds the navel and umbilical cord.
As shown in FIG. 3 The open flanged lips 22a-22b, surface area 10, orifice 25 and a combination of an upper and lower level FIG. 2 helps to move the umbilical cord in different directions during the cleaning procedures.
FIG. 3 the lower level from 22a to 22b is dimensioned 1.875 inches wide and 2.350 inches in length
FIG. 2 shows the upper level of the embodiment having upwardly extended sides 1 inch tall and a thickness ranging from 0.120 inches to 0.265 inches
Preferably the upper level shown in FIG. 2 and lower level shown in FIG. 3 are molded as a single unit by injection molding process.

DETAIL DESCRIPTION OF THE INVENTION

Figure 2:
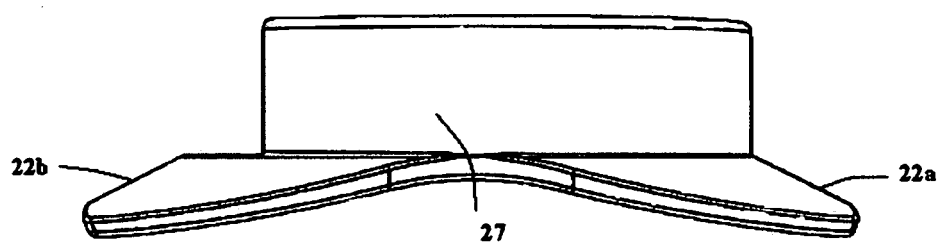
FIG. 2 showing upper level and lower level
Figure 3:
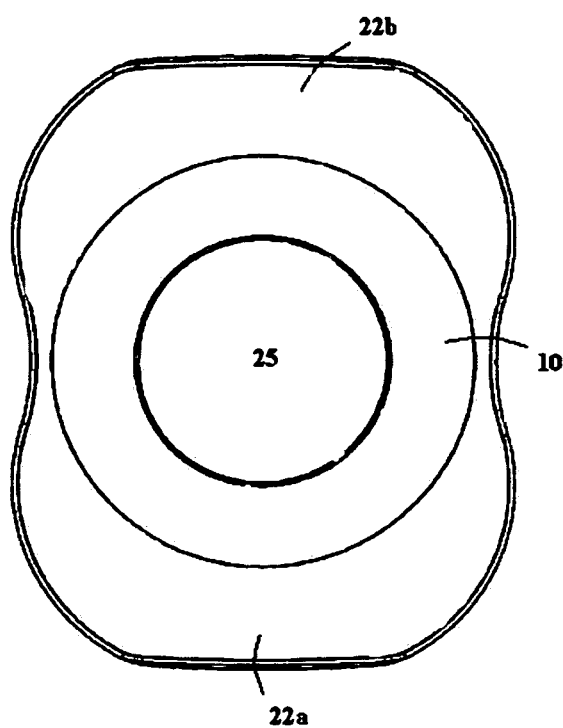
FIG. 3 A view of the lower level illustrating open Flanged lips 22a, 22b, Orifice 25 and surface area 10
Figure 4:
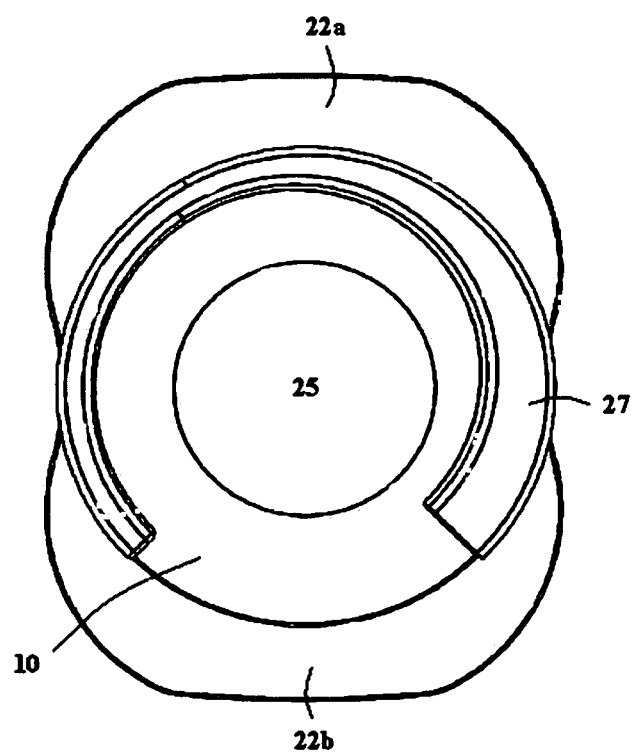
FIG. 4 Top view of the navel umbilical cord tab clearly showing detailed formation FIG. 5 A cross-sectional view taking along line A-A FIG. 6 Isometric view showing upper level with upwardly extended walls 27, "C" shape, and the relationship of the upper level with the lower level FIG. 7 Front view demonstrating direct access to the base of the navel.
Figure 5:
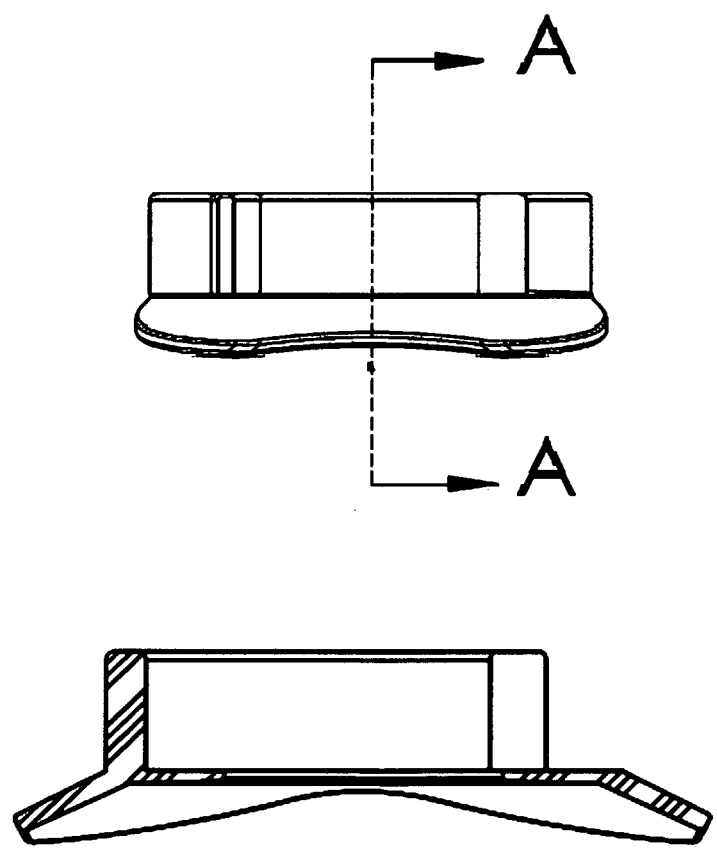
Figure 6:
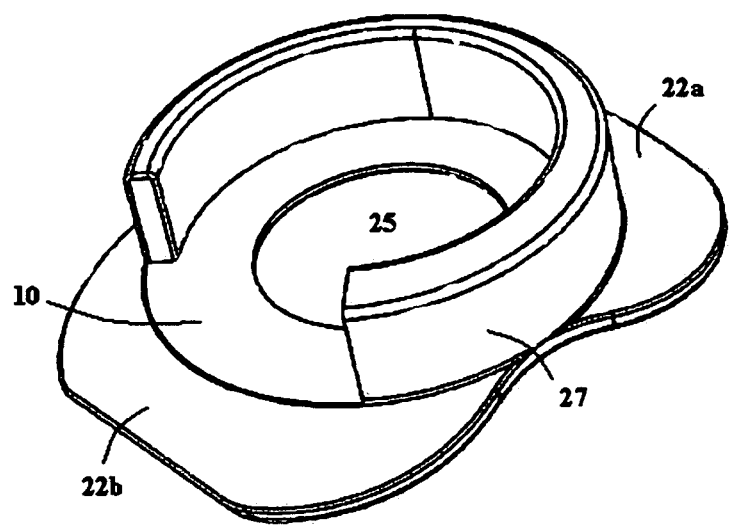
Figure 7:
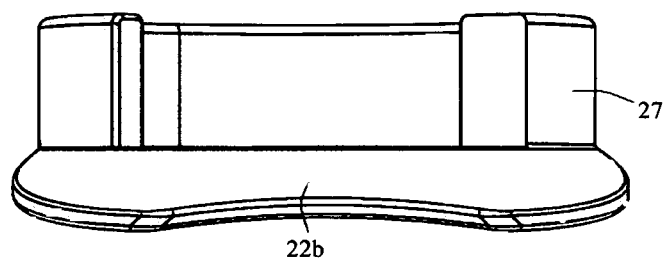

FIG. 2 the upper level forms a semi-circle on surface area 10 In this vicinity the surface area formed protects the baby's skin from direct contact with chemical used to clean the navel and umbilical cord.
FIG. 2 upper extended walls 27 works in accordance with surface area 10 and orifice 25 to control, support protect the navel, umbilical cord and during the cleaning procedure.
As shown FIG. 2 the upper level has a "C" shape. The opening of the "C" is about 1 inch wide with a 90 degree angle. This opening forms a path that allows the user easy access to the base of the navel and around umbilical cord.
The effectiveness of the "C" shaped FIG. 2 allows for the user's thumb to hold the tab securely in place with the middle or pointer finger.
The colors of the navel umbilical cord tab are ice blue, white and lavender.
It should be recognized that this invention is not limited to such dimension, material, or colors described herein

What I claim as my invention is:
1. A device that protects the skin surrounding an infant's navel from cleaning solutions, aids in manipulating the infant's umbilical cord, and provides support and protection to the infant's umbilical cord while a user cleans the infant's navel and umbilical cord, consisting of:
   a. a non-absorbent upper portion and a non-absorbent lower portion, the non-absorbent upper portion consisting of a wall extending upward from a junction of the non-absorbent lower portion and a base of the wall, the non-absorbent upper portion defining, by partially encircling a first area of the non-absorbent lower portion, the first area having a continuous solid surface and a central orifice that is completely encircled by the first area of the non-absorbent lower portion, having a second area less than the first area, wherein the partial encirclement of the first area by the wall defines an opening; and
   b. a third area of the non-absorbent lower portion, consisting of two flanges extending laterally outward from the first area at the junction of the base of the wall of the non-absorbent upper portion and the first area of the non-absorbent lower portion, each flange having a fourth area.
2. The device of claim 1, wherein the opening in the wall of the non-absorbent upper portion is about 1 inch.
3. The device of claim 1, wherein the dimension of the device measures 1.875 inches wide and 2.350 inches in length.
4. The device of claim 1, wherein the wall of the non-absorbent upper portion has a variable thickness ranging from 0.120 inches to 0.265 inches.
5. The device of claim 1, wherein the height of the wall of the non-absorbent upper portion is 1 inch.
6. The device of claim 1, wherein the central orifice is approximately 1 inch in diameter.
7. The device of claim 1, wherein the central orifice is circular.
8. The device of claim 1, wherein the non-absorbent lower portion is capable of protecting the skin surrounding an infant's navel from cleaning solutions while the infant's navel and umbilical cord are being cleaned.
9. The device of claim 1, wherein the non-absorbent upper portion is capable of protecting the infant's umbilical cord.
10. The device of claim 1, wherein the non-absorbent lower portion is capable of manipulating the infant's umbilical cord.
11. The device of claim 1, wherein the non-absorbent upper portion is capable of supporting the infant's umbilical cord.
12. The device of claim 1, wherein the user does not physically hold the infant's umbilical cord.

* * * * *